(12) United States Patent
Tao et al.

(10) Patent No.: US 11,293,875 B2
(45) Date of Patent: Apr. 5, 2022

(54) METHOD AND APPARATUS FOR CONTINUOUS GAS MONITORING USING MICRO-COLORIMETRIC SENSING AND OPTICAL TRACKING OF COLOR SPATIAL DISTRIBUTION

(71) Applicant: Arizona Board of Regents on behalf of Arizona State University, Scottsdale, AZ (US)

(72) Inventors: Nongjian Tao, Fountain Hills, AZ (US); Di Wang, Tempe, AZ (US); Chenwen Lin, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 358 days.

(21) Appl. No.: 16/142,463

(22) Filed: Sep. 26, 2018

(65) Prior Publication Data
US 2019/0094146 A1 Mar. 28, 2019

Related U.S. Application Data (60) Provisional application No. 62/564,143, filed on Sep. 27, 2017.

(51) Int. Cl.
*G01N 21/78* (2006.01)
*G01N 33/00* (2006.01)
*G01N 21/77* (2006.01)

(52) U.S. Cl.
CPC ....... *G01N 21/783* (2013.01); *G01N 33/0037* (2013.01); *G01N 33/0039* (2013.01);
(Continued)

(58) Field of Classification Search
CPC ............. G01N 21/783; G01N 33/0037; G01N 33/0039; G01N 33/0047; G01N 2021/7763; G01N 2021/7793; G01N 2201/0621
See application file for complete search history.

(56) References Cited

U.S. PATENT DOCUMENTS

| 4,205,043 A * | 5/1980 | Esch | G01N 31/224 116/206 |
|---|---|---|---|
| 4,904,449 A | 2/1990 | Heckmann | |

(Continued)

FOREIGN PATENT DOCUMENTS

| WO | 2008021614 A2 | 2/2008 |
|---|---|---|
| WO | 2008148025 A1 | 12/2008 |

(Continued)

OTHER PUBLICATIONS

Askim, Jon Robert. Portable colorimetric sensor array technology. Diss. University of Illinois at Urbana-Champaign, 2015. (Year: 2015).*

(Continued)

*Primary Examiner* — Robert J Eom
(74) *Attorney, Agent, or Firm* — Withrow & Terranova, P.L.L.C.

(57) ABSTRACT

A micro-colorimetric sensor for sensing target chemicals that converts time sequence information into a spatial distribution of color. By tracking the spatial color distribution, chemical exposure over time is thus detected, which overcomes the limitation of traditional colorimetric sensors. A porous media is coated on a top surface of the substrate. Multiple sensing chemicals are fused in parallel linear channels into the porous media coating. A plate is affixed over the substrate top surface to cover the plurality of parallel linear channels. An air sample is diffused along the porous media to get a clear pattern of spatial color distri-
(Continued)

bution and color images are captured. Optical parameters like gradient of spatial color distribution, intensity, and absorbance, etc., can be tracked to calculate analytes concentrations.

15 Claims, 10 Drawing Sheets

(52) U.S. Cl.
CPC . *G01N 33/0047* (2013.01); *G01N 2021/7763* (2013.01); *G01N 2021/7793* (2013.01); *G01N 2201/0621* (2013.01)

(56) References Cited

U.S. PATENT DOCUMENTS

| | | | |
|---|---|---|---|
| 5,192,500 A * | 3/1993 | Treddenick | G01N 21/783 422/408 |
| 7,132,837 B1 | 11/2006 | Tao | |
| 7,785,001 B2 | 8/2010 | Tao et al. | |
| 8,465,634 B2 | 6/2013 | Tao et al. | |
| 8,545,683 B2 | 10/2013 | Tao et al. | |
| 8,668,874 B2 | 3/2014 | Tao et al. | |
| 8,926,822 B2 | 1/2015 | Tao et al. | |
| 9,347,932 B2 | 5/2016 | Tao et al. | |
| 9,581,561 B2 | 2/2017 | Tao et al. | |
| 9,772,305 B2 | 9/2017 | Tao | |
| 9,909,993 B2 | 3/2018 | Tao et al. | |
| 9,931,055 B2 | 4/2018 | Forzani et al. | |
| 10,078,074 B2 | 9/2018 | Tsow et al. | |
| 10,143,401 B2 | 12/2018 | Tao et al. | |
| 10,209,232 B2 | 2/2019 | Forzani et al. | |
| 10,222,372 B2 | 3/2019 | Tao et al. | |
| 2005/0061056 A1 * | 3/2005 | Sunshine | G01N 29/022 73/23.2 |
| 2007/0235348 A1 | 10/2007 | Nagahara et al. | |
| 2012/0270330 A1 | 10/2012 | Tao et al. | |
| 2013/0115137 A1 | 5/2013 | Tao et al. | |
| 2014/0276104 A1 | 9/2014 | Tao et al. | |
| 2017/0038380 A1 | 2/2017 | Tao et al. | |
| 2017/0127988 A1 | 5/2017 | Tao et al. | |
| 2018/0140255 A1 | 5/2018 | Tao et al. | |
| 2018/0149598 A1 | 5/2018 | Tao et al. | |
| 2018/0156752 A1 | 6/2018 | Tao | |
| 2019/0082972 A1 | 3/2019 | Tao et al. | |
| 2019/0170748 A1 | 6/2019 | Tao et al. | |
| 2019/0239761 A1 | 8/2019 | Tao et al. | |
| 2019/0257802 A1 | 8/2019 | Forzani et al. | |

FOREIGN PATENT DOCUMENTS

| | | |
|---|---|---|
| WO | 2009064985 A1 | 5/2009 |
| WO | 2010030874 A1 | 3/2010 |
| WO | 2010036940 A2 | 4/2010 |
| WO | 2010141610 A1 | 12/2010 |
| WO | 2011031500 A2 | 3/2011 |
| WO | 2011140239 A2 | 11/2011 |
| WO | 2012047792 A2 | 4/2012 |
| WO | 2013019843 A2 | 2/2013 |
| WO | 2014052741 A1 | 4/2014 |
| WO | 2014116604 A1 | 7/2014 |
| WO | 2015102902 A2 | 7/2015 |
| WO | 2017156084 A2 | 9/2017 |
| WO | 2018057753 A1 | 3/2018 |
| WO | 2018170009 A1 | 9/2018 |
| WO | 2018187548 A2 | 10/2018 |
| WO | 2018213791 A2 | 11/2018 |
| WO | 2019136097 A1 | 7/2019 |

OTHER PUBLICATIONS

Choi, S-J. et al., "Selective Diagnosis of Diabetes Using Pt-Functionalized WO3 Hemitube Networks As a Sensing Layer of Acetone in Exhaled Breath", Analytical Chemistry, 2013 (available online Dec. 2012), vol. 85, No. 3, pp. 1792-1796 <DOI: 10.1021/ac303148a>.

Cui, S. et al., "Ultrahigh sensitivity and layer-dependent sensing performance of phosphorene-based gas sensors", Nature Communications, Oct. 2015, vol. 6, article 8632, 9 pages <DOI:10.1038/ncomms9632>.

Dräger Safety AG & Co. KGAA, "Drager-Tubes & CMS-Handbook: Soil, Water, and Air Investigations as well as Technical Gas Analysis", 16th edition, 2011, p. 225.

EPA, "National Ambient Air Quality Standards Table", United States Environmental Protection Agency, Jul. 2016 [retrieved on Sep. 23, 2019 from archive.org, as it appeared on Aug. 14, 2016], retreived from the internet: <https://web.archive.org/web/20160814034808/https://www.epa.gov/criteria-air-pollutants/naaqs-table>.

Guan, Y. et al., "Kinetics of small molecule interactions with membrane proteins in single cells measured with mechanical amplification", Science Advances, Oct. 2015, vol. 1, No. 9, article e1500633, 8 pages <DOI:10.1126/sciadv.1500633>.

Kamionka, M. et al., "Calibration of a multivariate gas sensing device for atmospheric pollution measurement", Sensors and Actuators B: Chemical, Oct. 2006, vol. 118, No. 1-2, pp. 323-327 <DOI:10.1016/j.snb.2006.04.058>.

Korotcenkov, G. et al., "Ozone measuring: What can limit application of SnO2-based conductometric gas sensors?", Sensors and Actuators B: Chemical, Jan. 2012, vol. 161, No. 1, pp. 28-44 <DOI:10.1016/j. snb.2011.12.003>.

Lelieveld, J. et al., "The contribution of outdoor air pollution sources to premature mortality on a global scale", Nature, Sep. 2015, vol. 525, No. 7569, pp. 367-371 <DOI:10.1038/nature15371>.

Li, J. et al., "Carbon Nanotube Sensors for Gas and Organic Vapor Detection", Nano Letters, Jun. 2003, vol. 3, No. 7, pp. 929-933 <DOI:10.1021/nl034220x>.

Lim, S. et al., "A comparative risk assessment of burden of disease and injury attributable to 67 risk factors and risk factor clusters in 21 regions, 1990-2010: a systematic analysis for the Global Burden of Disease Study 2010", The Lancet, 2012, vol. 380, No. 9859, pp. 2224-2260 <DOI:10.1016/S0140-6736(12)61766-8>.

Mazzone, P. et al., "Lung Cancer Diagnosis by the Analysis of Exhaled Breath with a Colorimetric Sensor Array", Thorax, 2007, vol. 62, No. 7, pp. 565-568 <DOI:10.1136/thx.2006.072892>.

Mills, N. et al., "Adverse cardiovascular effects of air pollution", Nature Clinical Practice Cardiovascular Medicine, Jan. 2009, vol. 6, No. 1, pp. 36-44 <DOI:10.1038/ncpcardio1399>.

Mondal, S. et al., "Development of high sensitivity potentiometric NOx sensor and its application to breath analysis", Sensors and Actuators B: Chemical, Nov. 2011, vol. 158, No. 1, pp. 292-298 <DOI:10.1016/j.snb.2011.05.063>.

Nakano, N. et al., "An automatic monitor of formaldehyde in air by a monitoring tape method", Journal of Environmental Monitoring, Jun. 1999, vol. 1, No. 3, pp. 255-258.

Pang, X. et al., "Electrochemical ozone sensors: A miniaturised alternative for ozone measurements in laboratory experiments and air-quality monitoring", Sensors and Actuators B: Chemical, Mar. 2017, vol. 240, pp. 829-837 <DOI:10.1016/j.snb.2016.09.020>.

Peterson, P. et al., "Practical Use of Metal Oxide Semiconductor Gas Sensors for Measuring Nitrogen Dioxide and Ozone in Urban Environments", Sensors, Jul. 2017, vol. 17, No. 7, 25 pages <DOI:10.3390/s17071653>.

Qin, X. et al., "A Colorimetric Chemical Sensing Platform for Real-Time Monitoring of Indoor Formaldehyde", IEEE Sensors Journal, Mar. 2015 (Date of Publication: Oct. 2014), vol. 15, No. 3, pp. 1545-1551 <DOI:10.1109/JSEN.2014.2364142>.

Rakow, N. et al., "A colorimetric sensor array for odour visualization", Nature, Aug. 2000, vol. 406, pp. 710-713.

Saxon, A. et al., "Air pollution and allergy: you are what you breathe", Nature Immunology, Mar. 2005, vol. 6, No. 3, pp. 223-226 <DOI:10.1038/ni0305-223>.

(56) References Cited

OTHER PUBLICATIONS

Takeuchi, K. et al., "Quantitative determination of aqueous-phase ozone by chemiluminescence using indigo-5, 5'-disulfonate". Analytical Chemistry, Mar. 1989, vol. 61, No. 6, pp. 619-623 <DOI:10.1021/ac00181a025>.

Tsow, F. et al., "Frequency-coded chemical sensors", Analytical Chemistry, Dec. 2007, vol. 80, No. 3, pp. 606-611 <DOI:10.1021/ac7016162>.

Tsujita, W. et al., "Gas sensor network for air-pollution monitoring", Sensors and Actuators B: Chemical, Oct. 2005, vol. 110, No. 2, pp. 304-311 <DOI:10.1016/j.snb.2005.02.008>.

Wang, H. et al., "Determining electrochemical surface stress of single nanowires", Angewandte Chemie International Edition, 2017, vol. 56, No. 8, pp. 2132-2135 <DOI:10.1002/anie.201611297>.

Wang, R. et al., "A Microfluidic-Colorimetric Sensor for Continuous Monitoring of Reactive Environmental Chemicals", IEEE Sensors Journal, May 2012 (Date of Publication: Oct. 2011), vol. 12, No. 5, pp. 1529-1535 <DOI:10.1109/JSEN.2011.2174218>.

Wetchakun, K. et al., "Semiconducting metal oxides as sensors for environmentally hazardous gases", Sensors and Actuators B: Chemical, Dec. 2011, vol. 160, No. 1, pp. 580-591 <DOI:10.1016/j.snb.2011 08.032>.

Xing, R. et al., "Preparation and Gas Sensing Properties of In2O3/Au Nanorods for Detection of Volatile Organic Compounds in Exhaled Breath", Scientific Reports, Jun. 2015, vol. 5, article 10717, 14 pages <DOI:10.1038/srep10717>.

Yamazoe, N., "Toward innovations of gas sensor technology", Sensors and Actuators B: Chemical, Jul. 2005, vol. 108, No. 1-2, pp. 2-14 <DOI:10.1016/j.snb.2004.12.075>.

\* cited by examiner

METHOD AND APPARATUS FOR CONTINUOUS GAS MONITORING USING MICRO-COLORIMETRIC SENSING AND OPTICAL TRACKING OF COLOR SPATIAL DISTRIBUTION

CROSS-REFERENCE TO RELATED APPLICATION

This application is a non-provisional application of currently U.S. Provisional Patent Application No. 62/564,143, filed Sep. 27, 2017, entitled "METHOD AND APPARATUS FOR CONTINUOUS MONITORING OF OZONE USING MICRO-COLORIMETRIC SENSING AND OPTICAL EDGE-TRACKING," to the same inventors herein and claims the priority benefit of that filing date. Application No. 62/564,143 is incorporated by reference.

STATEMENT REGARDING FEDERALLY SPONSORED RESEARCH OR DEVELOPMENT

This invention was made with government support under U01 EB021980 awarded by the National Institutes of Health. The government has certain rights in the invention.

TECHNICAL FIELD

The present invention relates to a method and apparatus for continuous gas monitoring using micro-colorimetric sensing and optical tracking of color spatial distribution. More particularly, the method and apparatus utilize chemical diffusion in a medium, reaction of the chemical with a component in the medium to produce a distinct color change, and spatial distribution of the color change with a CMOS imager and imaging processing algorithm.

BACKGROUND

The detection of airborne chemicals is critical to many applications, such as air quality monitoring and environmental health studies [1-4]. It has motivated increasing efforts to develop miniaturized and low-cost chemical gas sensors with high performance [5-10]. These sensors include metal oxide semiconductors [11-13] and electrochemical sensors [14-16], but they suffer from poor selectivity, limitation to a single analyte in one sensor, high power consumption and need of frequent calibrations. Colorimetric sensors, as another type of well-known and widely used gas sensor, rely on employing sensing chemicals that change colors upon chemical reactions with target analytes. The chemical reactions are often specific, making colorimetric sensors particularly selective for detection of the target analytes. However, the chemical reactions are usually irreversible. For this reason, most colorimetric sensors are for one-time use only, and lack the capability for continuous monitoring of analytes[17][18, 19].

One approach to overcome the above issue of colorimetric sensors is to use a roll of a sensor strip like a cassette player or a roll of film in traditional cameras [20]. When an exposed area is expired, a fresh sensing area from the roll is exposed to analytes, such that the sensor can detect an analyte at different time points. Alternative approach to prolong a sensor's lifetime to control the flow of sample air to the sensor with an air pump [21].

Figure 1:
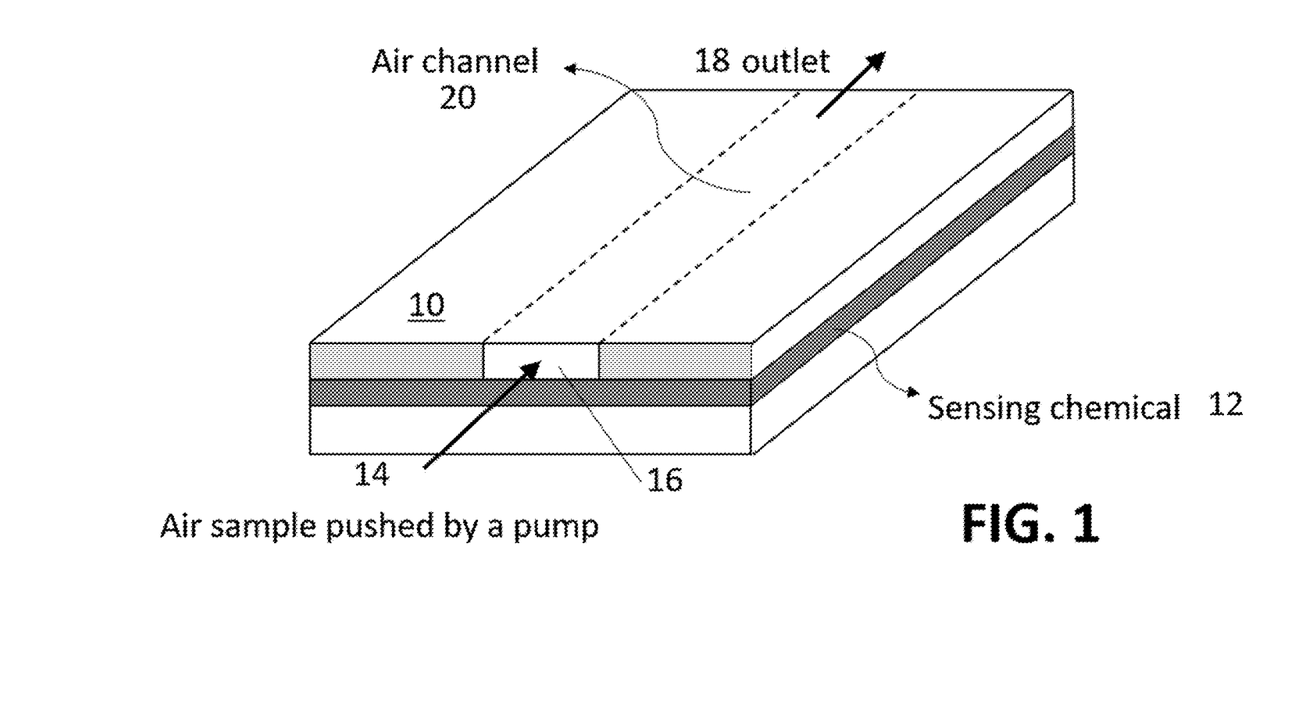
FIG. 1 shows a single air channel created on a surface coated with a sensing material of the prior art.

As illustrated in FIG. 1, another approach by the inventors was to overcome the one-time use limitation described above, the inventors' group previously developed a fluidics-based colorimetric sensor [22]. It coats a solid surface 10 (e.g., paper or glass) with a sensing chemical 12 that reacts with a target chemical in air and produce a color change [22, 23]. A narrow air channel 20 with an inlet 16 and an outlet 18 is created on top of the surface, and an air pump (not shown) is used to force air sample 14 to flow along the air channel 20 from the inlet 16 to the outlet 18. The target chemical in air (e.g., $NO_2$ and $O_3$) reacts with the sensing chemical on the surface near the inlet first. After depletion of the sensing chemical near the inlet, the reaction between the target chemical and the sensing material move along the channel towards the outlet, and eventually reaches the channel end when the sensing chemical along the entire channel is depleted. This previous work provides a possibility for detecting airborne chemicals over a certain time period, which is a major advantage compared with traditional colorimetric sensor that provides one time reading only.

However, all the methods mentioned above use a mechanical motor to rotate the roll of the sensor strip, or a pump to force air flow along the air channel, which adds cost to the device, increases energy consumption and device size, and requires periodic replacement or calibration. More seriously, the inventors herein found that most mechanical motors or pumps tend to wear and degrade over time, which causes the rotation speed and flow rate to vary over time. Because the reaction rate depends on the rotation speed and flow rate in the known devices, respectively, errors are inevitable for chemical sensing using the above approaches. The fluidics-based colorimetric sensor described above has several other limitations. First, diffusion of chemicals in air is fast along the channel. Consequently, the sensed chemical along the channel is depleted quickly, and lifetime of the sensor is short, especially when the target chemical concentration is high. This is problematic for applications directed to monitoring air quality over an extensive period of time, such as days and weeks. Another drawback is that fabrication of the air channel with precise dimensions and airtight sealing is difficult. Next, there is no clear pattern of color spatial distribution to track, like a sharp color gradient, due to the fast gas diffusion through the air channel. Further, the device is limited to detecting only one chemical.

Another approach like the fluidics-based colorimetric sensor uses non-linear sensing paths [24]. In this case barriers at channel boundaries cannot be omitted, which increases the fabrication difficulty. Otherwise gases will diffuse to different parts of each channel simultaneously instead of the predetermined direction, losing the benefit of long lifetime.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A micro-colorimetric sensor for sensing target chemicals using optical tracking includes a substrate. A porous media is coated on a top surface of the substrate. Multiple sensing chemicals are fused in parallel linear channels into the porous media coating. A plate is affixed over the substrate top surface to cover the plurality of parallel linear channels. An air sample is diffused along the porous media to get a clear pattern of spatial color distribution and color images are captured. Optical parameters like gradient of spatial color distribution, intensity, and absorbance, etc., can be tracked to calculate analytes concentrations.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes a method and apparatus for continuous monitoring and quantitative analysis of airborne chemicals. Several features of methods and devices in accordance with example embodiments are set forth and described in the figures. It will be appreciated that methods and devices in accordance with other example embodiments can include additional procedures or features different than those shown in the figures. Example embodiments are described herein with respect to a method and apparatus that utilizes chemical diffusion in a medium, reaction of the chemical with a component in the medium to produce a distinct color change, and spatial distribution of the color change with a CMOS imager. In one example, the apparatus monitors multiple airborne chemicals continuously over time, thus overcoming the limitations of traditional colorimetric sensing methods. However, it will be understood that these examples are for the purpose of illustrating the principles, and that the invention is not so limited.

Unless the context requires otherwise, throughout the specification and claims which follow, the words "comprise" or "include" and variations thereof, such as, "comprises" or "includes" and "comprising" or "including" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the example is included in at least one example of the present disclosure. Thus, the appearances of the phrases "in one example" or "in an example" in various places throughout this specification are not necessarily all referring to the same example or embodiment. Furthermore, the particular features, structures, or characteristics may be combined in any suitable manner in one or more examples or embodiments.

Definitions

Generally, as used herein, the following terms have the following meanings when used within the context of quantitative analysis of airborne chemicals:

The articles "a" or "an" and the phrase "at least one" as used herein refers to one or more.

As used herein, "plurality" is understood to mean more than one. For example, a plurality refers to at least two, three, four, five, ten, 25, 50, 75, 100, 1,000, 10,000 or more.

As used in this specification, the terms "computer", "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

"Obtaining" is understood herein as manufacturing, purchasing, or otherwise coming into possession of.

Example Embodiments

Figure 2:
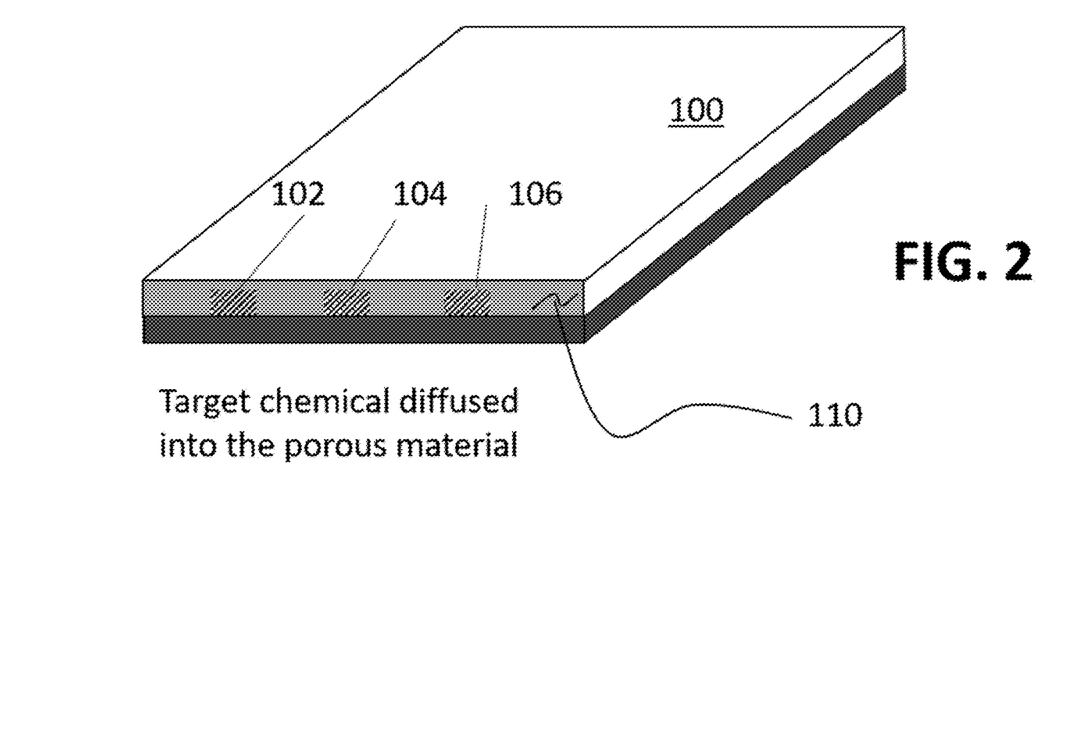
FIG. 2 shows an example of fabricated parallel linear channels in porous media.

Referring now to FIG. 2, an example of a micro-colorimetric sensor is shown. wherein parallel linear channels of porous media are fabricated. A micro-colorimetric sensor 100 includes a plurality of parallel linear channels of porous media 102, 104, 106. Each linear channel includes a sensing material for one or several specific target chemicals in air. Each line can be separated by material 110 or can be next to each other. In some examples the porous media is selected from the group consisting of silica gel, cellulose, polymers, porous glass, silicon, metal oxides, metal nitrides, zeolites and combinations thereof.

Each of the sensing chemicals is selected for a particular target chemical, so that the sensor can simultaneously detect multiple chemicals. Air sample diffuses passively along each linear channel without using a pump, and the target chemical in the air sample reacts with the sensing chemical in the linear channel, starting from the inlet, which creates a color gradient that moves from the inlet towards to the channel end. Because air diffusion in the porous media is substantially slower than that in air, the color gradient is sharp and moves slowly along the linear channel, which prolongs the lifetime of the sensor, and allows continuous monitoring of chemicals over a long time. Rates of diffusion and reaction can be controlled by predetermined porous media and its porosity, and amount of sensing chemicals loaded, so that barriers between channels are not always necessary to prevent fast diffusion from the channel sideway. The slowly moving color gradient associated with passive diffusion creates a challenge to accurately track the moving color gradient. This difficulty is overcome by introducing a color gradient tracking imaging processing algorithm, which can track the moving speed of the color gradient in each linear channel. The moving speed of the color gradient reflects the concentration of the target chemical. Other optical parameters like intensity and absorbance, etc., can also be used to calculate analytes concentrations. In other examples, the tracking imaging processing algorithm is selected from the group consisting of tracking intensity or absorbance change of the whole or part of the image, tracking the moving of intensity or absorbance pattern of the whole or part of the image where the pattern includes point, corner, edge, and block and combinations thereof.

Figure 3A:
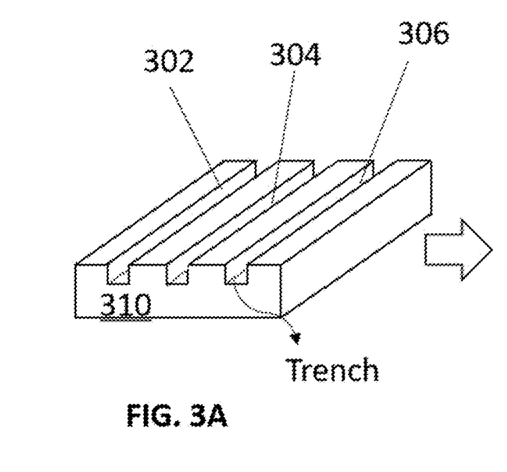
FIG. 3A-FIG. 3C show an example of a sensor in various stages of manufacture.
Figure 3B:
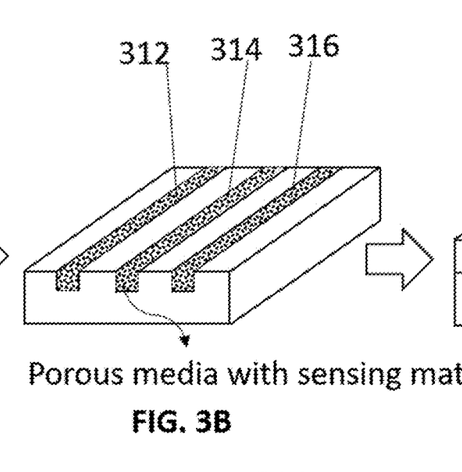
Figure 3C:
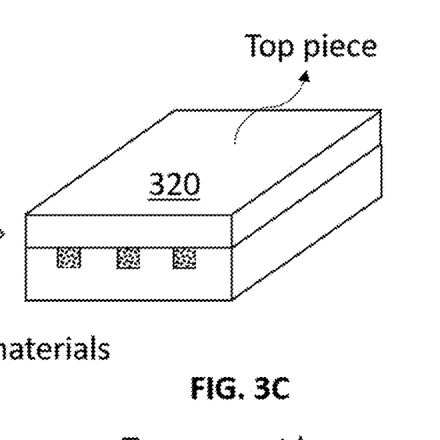

Referring now to FIG. 3A-FIG. 3C, an example of a sensor in various stages of manufacture is shown. Referring now particularly to FIG. 3A, in one example, parallel trenches 302, 304, 306 are first created in a solid substrate 310. Next, as shown in FIG. 3B, porous media 312, 314, 316 with embedded sensing materials are then used to fill the trenches. The porous media may each be embedded with the same or different sensing materials. After filling the trenches with the porous media a plate 320 is used to cover the trenches and the solid substrate 310. The trenches are formed in parallel in the substrate to allow detection of multiple analytes. The substrate and cover cooperate to form barriers between the trenches to eliminate chemical diffusion from one trench linear channel to another. There are multiple ways that one can create such a barrier.

Figure 4A:
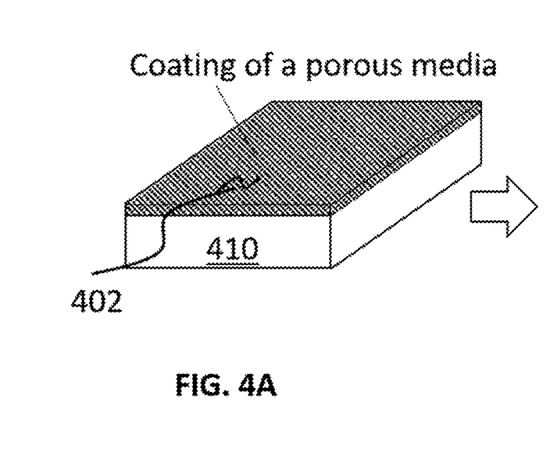
FIG. 4A-FIG. 4C show an alternative example of a sensor in various stages of manufacture.
Figure 4B:
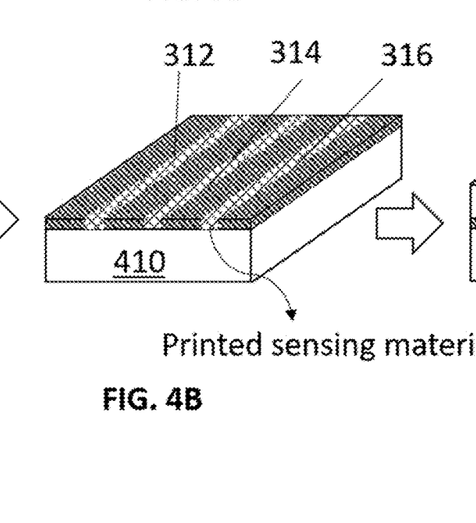
Figure 4C:
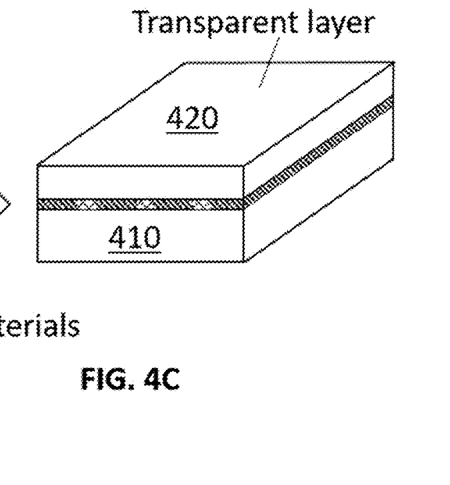

Referring now to FIG. 4A-FIG. 4C an alternative example of a sensor in various stages of manufacture is shown. Referring particularly to FIG. 4A, a porous media 402 is coated on a top surface of solid substrate 410. Next, multiple sensing chemicals 412, 414, 416 are fused in parallel linear channels into the porous media coating as shown in FIG. 4B. Then, as shown in FIG. 4C, a material 420 is placed on top of the porous media 402.

Examples

Example 1 Continuous Monitoring of Ozone Using Micro-Colorimetric Sensing and Optical Edge-Tracking One example of micro-colorimetric sensor for continuous $O_3$ monitoring was manufactured by a porous media and chemically responsive compounds. The porous media in this example was silica gel plate, purchased from Sorbent Technologies (Polyester backed silica G TLC plates). The silica gel plate was cut into 0.5 mm (width)×4 mm (length) small pieces and immersed in an aqueous solution with formulation of Indigo carmine and citric acid. Following by a 2-hour vacuum drying process, the micro-colorimetric $O_3$ sensor was then covered with a piece of Acrylic and fixed by screws. The micro-colorimetric sensor was illuminated with a white LED (LEDtronics Inc.) and imaged with a CMOS imager (Logitech, Inc.) for real-time monitoring of the color progression continuously when exposed to $O_3$ (FIG. 1a).

Example 2

Micro-Colorimetric Sensor Array for Detection of Nitrogen Dioxide, Ozone, and Formaldehyde.

Figure 10A:
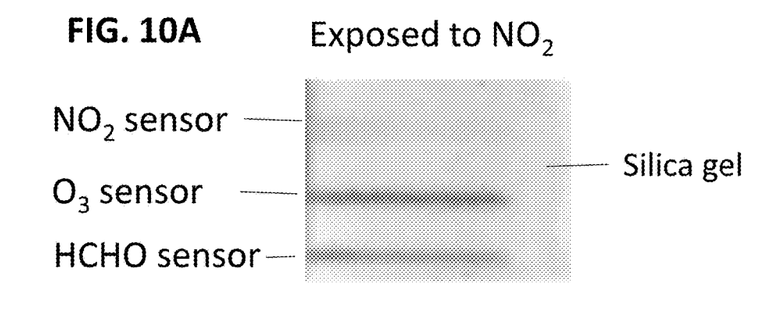
FIG. 10A shows an example of an image of a micro-colorimetric sensor array showing color gradient developed on $NO_2$ sensing channel after exposed to $NO_2$.
Figure 10B:
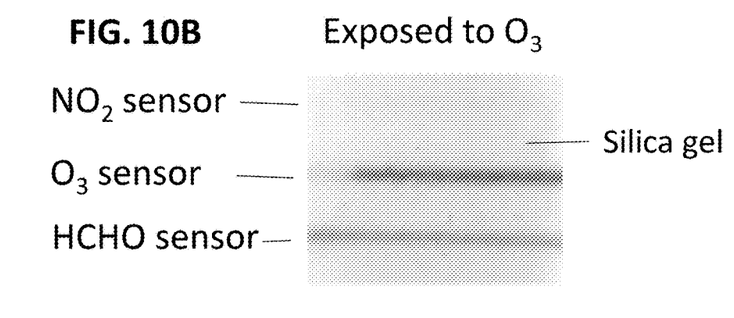
FIG. 10B shows an example of an image of a micro-colorimetric sensor array showing color gradient developed on $O_3$ sensing channel after exposed to $O_3$.
Figure 10C:
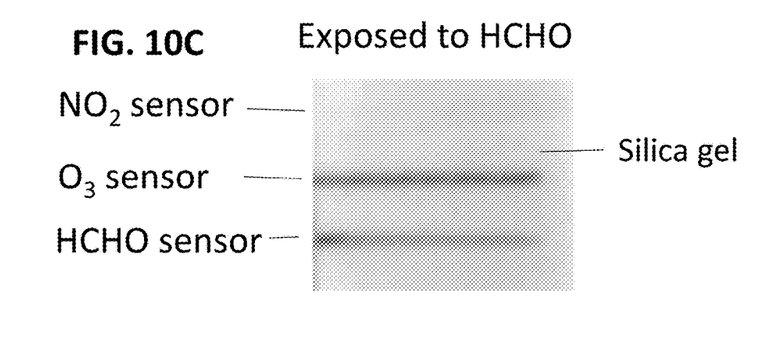
FIG. 10C shows an example of an image of a micro-colorimetric sensor array showing color gradient developed on HCHO sensing channel after exposed to HCHO.

One example of micro-colorimetric sensor array for detection of Nitrogen Dioxide, Ozone, and Formaldehyde was fabricated by inkjet printing method. Silica gel was used as porous media and coated on polyester substrate. Three sensing solutions containing N,N-dimethyl-1naphthylamine, indigo carmine, and hydroxylamine sulfate respectively were prepared for selective detection of nitrogen dioxide, ozone, and formaldehyde. The three sensing solutions were inkjet printed on the porous silica gel layer in the form of three parallel lines. An acrylic plate was then affixed over the top surface of the porous silica layer to cover the three parallel linear channels. FIG. 10 are top views of the sensor array after exposing to ozone, nitrogen dioxide, and formaldehyde. Each sensing channel changed color and a clear color gradient was generated after exposing to the corresponding analyte, and there is no obvious cross talking between different sensing channels.

Figure 5A:
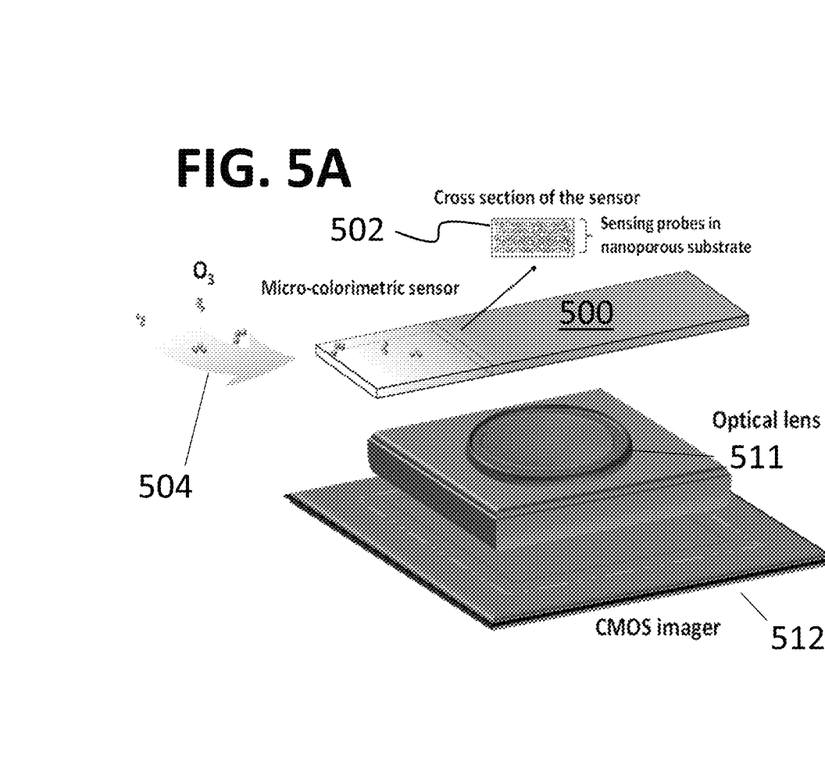
FIG. 5A shows an example of schematics of a micro-colorimetric sensing system.

Referring now to FIG. 5A, an example of schematics of a micro-colorimetric sensing system is shown. Colorimetric sensors are typically made for one-time use only because of the irreversible chemical reactions that produce color changes. To overcome this limitation, a micro-colorimetric sensing platform 500 was used to track color changes associated with the chemical reaction of $O_3$ with the sensing probes 502 located along the sensor. The micro-colorimetric sensing platform 500 was made substantially as described hereinabove. To minimize both the cost and size of the device, a passive sample delivery method 504, which relied on diffusion of air sample from the inlet to the end of the micro-colorimetric sensor was used, rather than using an air pump. Color images of the sensor were obtained using an optical lens 511 coupled to a CMOS imager 512.

Figure 5B:
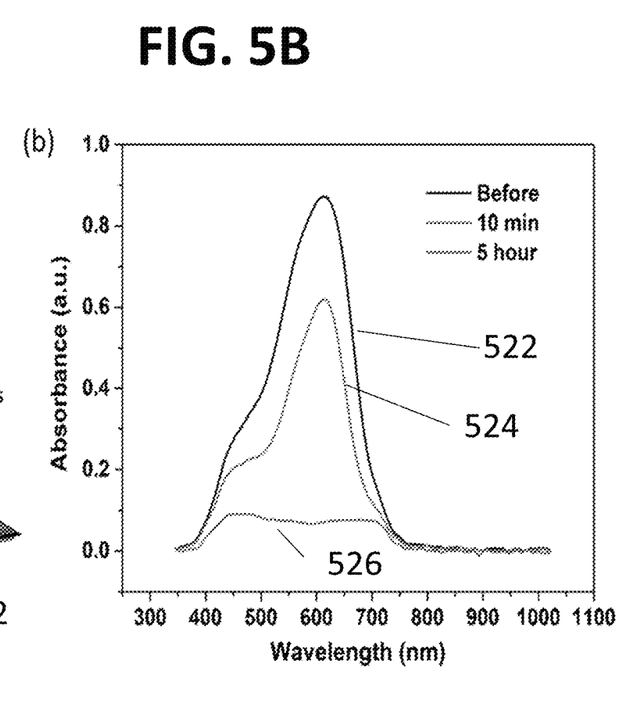
FIG. 5B shows a plot of UV vs. spectra of indigo carmine ($O_3$ sensing probe) on silica paper substrate before and after exposure to $O_3$.

Referring now to FIG. 5B, an example shows a plot of UV vs. spectra of indigo carmine ($O_3$ sensing probe) on silica paper substrate before and after exposure to $O_3$. Absorbance in a.u. is plotted on the Y-axis and wavelength in nm is plotted on the X-Axis. Plot 522 represents data from images before exposure to $O_3$. Plot 524 represents data from images after 10 minutes of exposure. Plot 526 represents data from images after five hours of exposure.

Figure 6A:
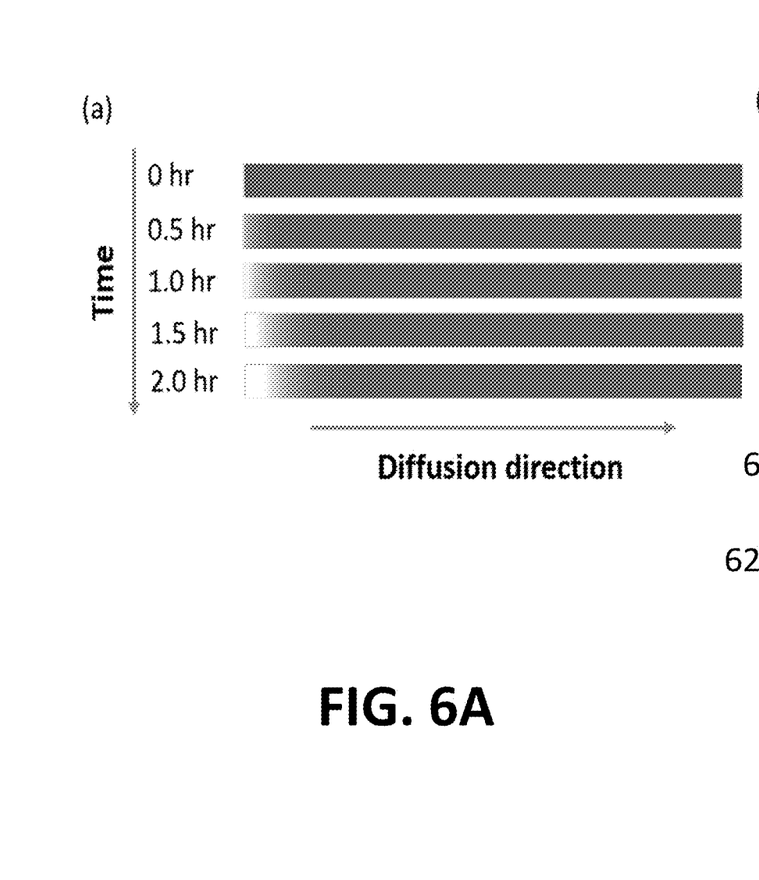
FIG. 6A shows an example of simulated concentration profiles of unreacted $O_3$ sensing probe from sensor inlet when exposed to 500 ppbV $O_3$ for 0, 0.5, 1, 1.5 and 2 hours, respectively.

To guide the design of the sensor, diffusion and chemical reaction kinetics were simulated along the micro-colorimetric sensor numerically. FIG. 6A shows simulated concentration profiles of an unreacted $O_3$ sensing probe from sensor inlet when exposed to 500 ppbV $O_3$ for 0, 0.5, 1, 1.5 and 2 hours, respectively is shown. The simulation referenced above shows that color changes when exposing the sensor to 500 ppbV $O_3$ for different time durations. Note that the shaded bars represent the cross section of a micro-colorimetric sensor along the direction from the inlet and the white color section 602 represents the consumption of the sensing probe at a specific location along the sensor.

In one example, a micro-colorimetric $O_3$ sensor was placed in a test chamber with defined temperature and humidity, and $O_3$ sample gas was introduced into the chamber, which diffused into the sensor. When $O_3$ enters a micro-colorimetric sensor, it reacts with $O_3$ sensing probe near the inlet initially, and then with the probe along the micro-colorimetric sensor over time as the sensing probe near the inlet is consumed upon irreversible reaction with $O_3$. The color of reacted area changed from blue to very light yellow. The CMOS imager monitors the local reaction (color change) along the sensor, and the optical edge-tracking technique allows real-time tracking of the color progression along the sensor thus enables continuous detection of $O_3$.

Figure 6B:
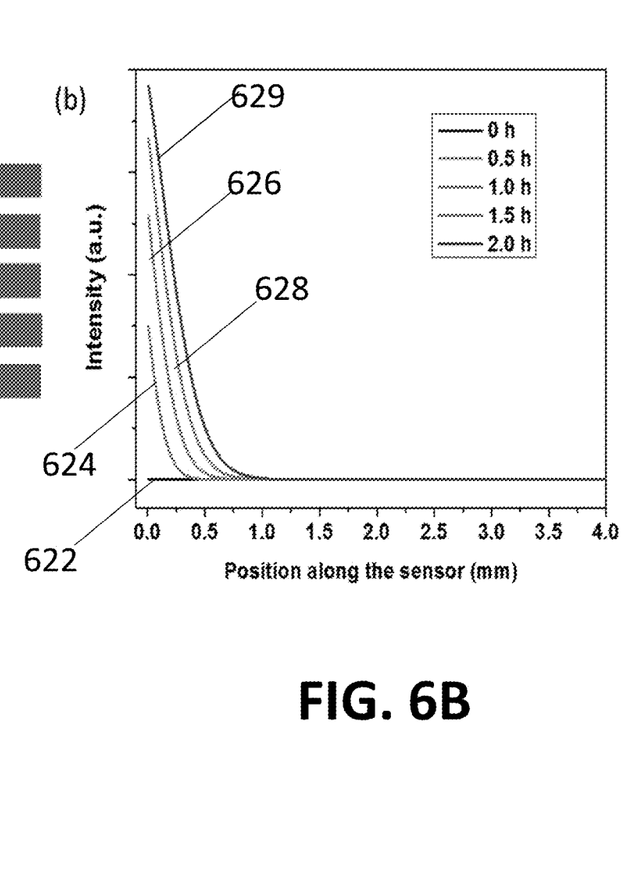
FIG. 6B shows an example of simulated intensity profile along the sensor from the inlet over time.
Figure 6C:
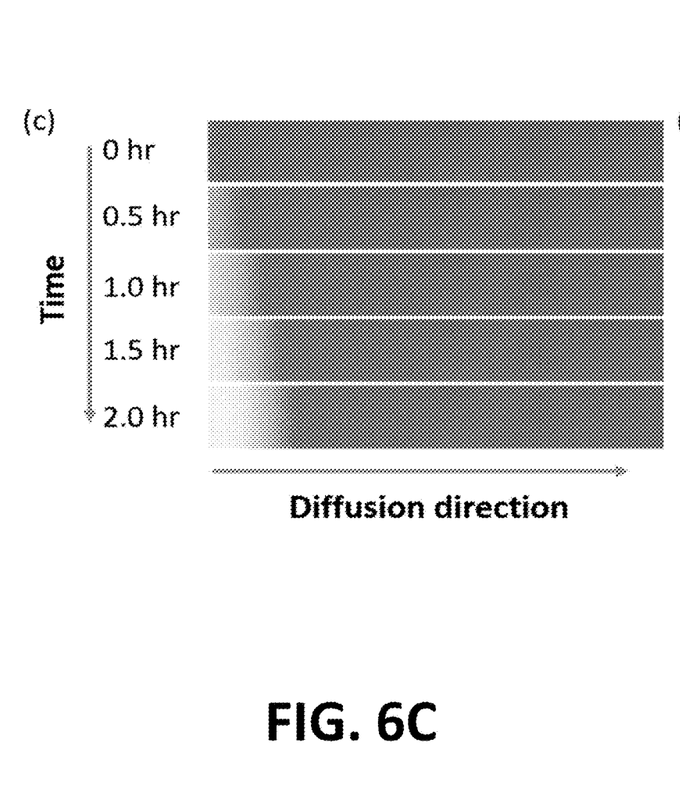
FIG. 6C shows an example of measured images with the CMOS imager showing color gradient development over 2 hours at 500 ppb $O_3$.

Referring now to FIG. 6C, an example of measured images with the CMOS imager showing color gradient development over 2 hours at 500 ppb $O_3$ is shown. To experimentally validate the micro-colorimetric sensor for continuously monitoring of $O_3$, the sensor was tested by exposing the sensor to 500 ppbV $O_3$ over 2 hours, and observed gradual color development along the sensor. The measured color changes at different locations over time (shown in FIG. 6D) are consistent with the simulated results in FIG. 6B, and the simulation and experiment also show that the micro-colorimetric sensor with passive sampling can continuously track $O_3$ in the air.

Figure 6D:
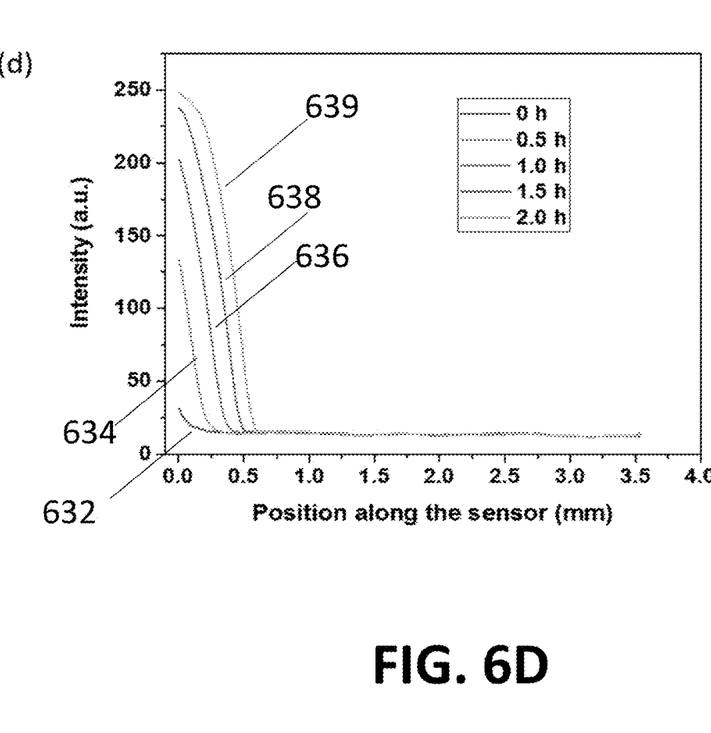
FIG. 6D shows an example of measured intensity changes along the sensor from the inlet over time.

Referring now to FIG. 6D, an example of measured intensity changes along the sensor from the inlet to outlet over time is shown. Intensity in a.u. is plotted on the Y-axis and position along the sensor in nm is plotted on the X-Axis. Plot 632 represents data from images at the instant of exposure to $O_3$. Plot 634 represents data from images after 30 minutes of exposure. Plot 636 represents data from images after one hour of exposure. Plot 638 represents data from images after 1.5 hours of exposure and plot 639 represents data from images after two hours of exposure.

Referring now to FIG. 6D, an example of measured intensity changes along the sensor from the inlet over time is shown. Intensity in a.u. is plotted on the Y-axis and position along the sensor in nm is plotted on the X-Axis. Plot 632 represents data from images at the instant of exposure to $O_3$. Plot 634 represents data from images after 30 minutes of exposure. Plot 636 represents data from images after one hour of exposure. Plot 638 represents data from images after 1.5 hours of exposure and plot 639 represents data from images after two hours of exposure.

The test results of traditional colorimetric sensors such as detector tubes usually read by naked-eye. This method is not accurate and not adequate for a micro-colorimetric sensor. To overcome this difficulty, a sensitive CMOS imager was used in the device to obtain high quality images and fundamentally improve the sensitivity and detection limit. To further improve the sensitivity, an optical edge tracking technique has been developed. Several optical edge tracking methods have been reported to highly improve the detection limit (e.g., cell movement, nanowires surface stress, etc.) [27, 28].

Figures 7A, 7B:
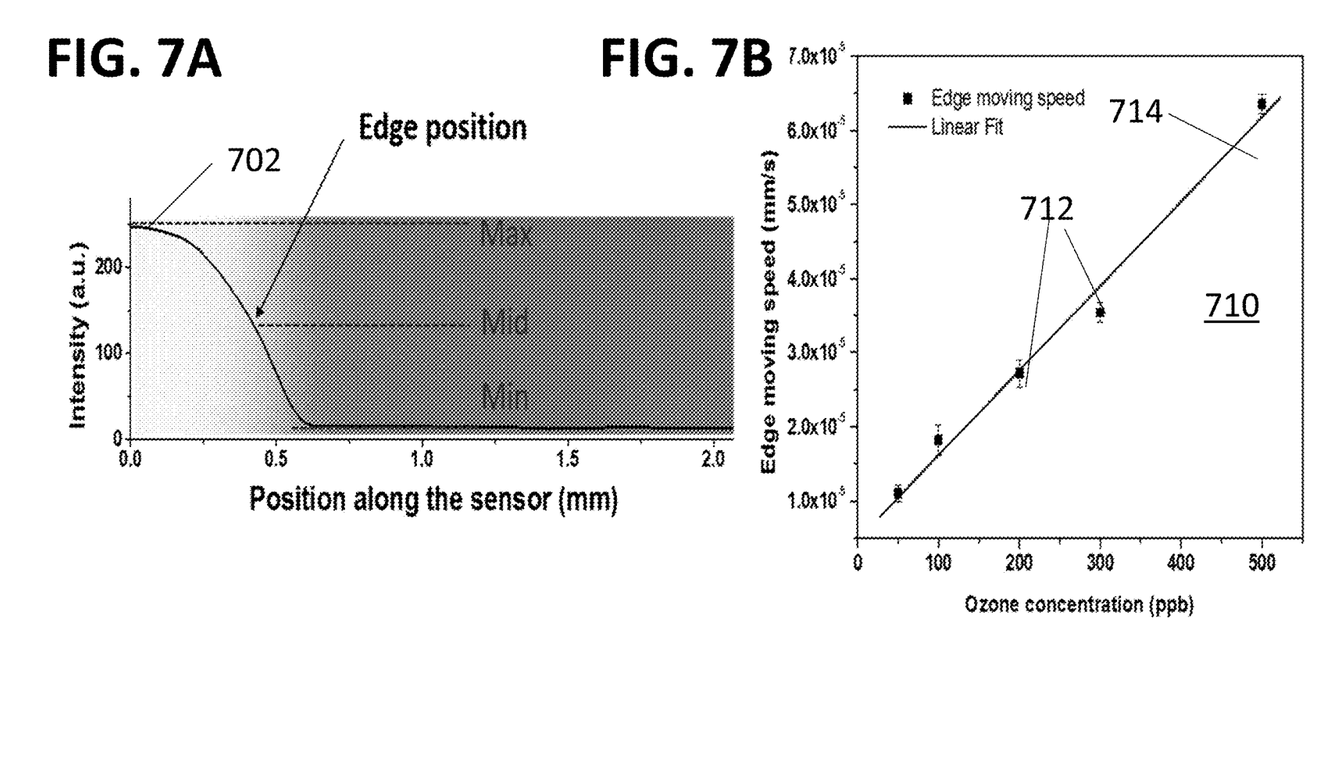
FIG. 7A shows an example of an image of a partial reacted sensor and corresponding intensity profile of the sensor.
FIG. 7B shows an example of calibration of the micro-colorimetric $O_3$ sensor with a reference $O_3$ analyzer, showing a linear dependence of the sensor response (edge moving speed) to $O_3$ concentration.

FIG. 7A shows an example of an image of a partial reacted sensor and corresponding intensity profile of the sensor. The optical edge tracking method finds the maximum (Max) and minimum (Min) value to calculate the mid value and searches the position along the sensor that has the intensity value closest to Mid, and finally defines the position as the "edge".

Figure 8:
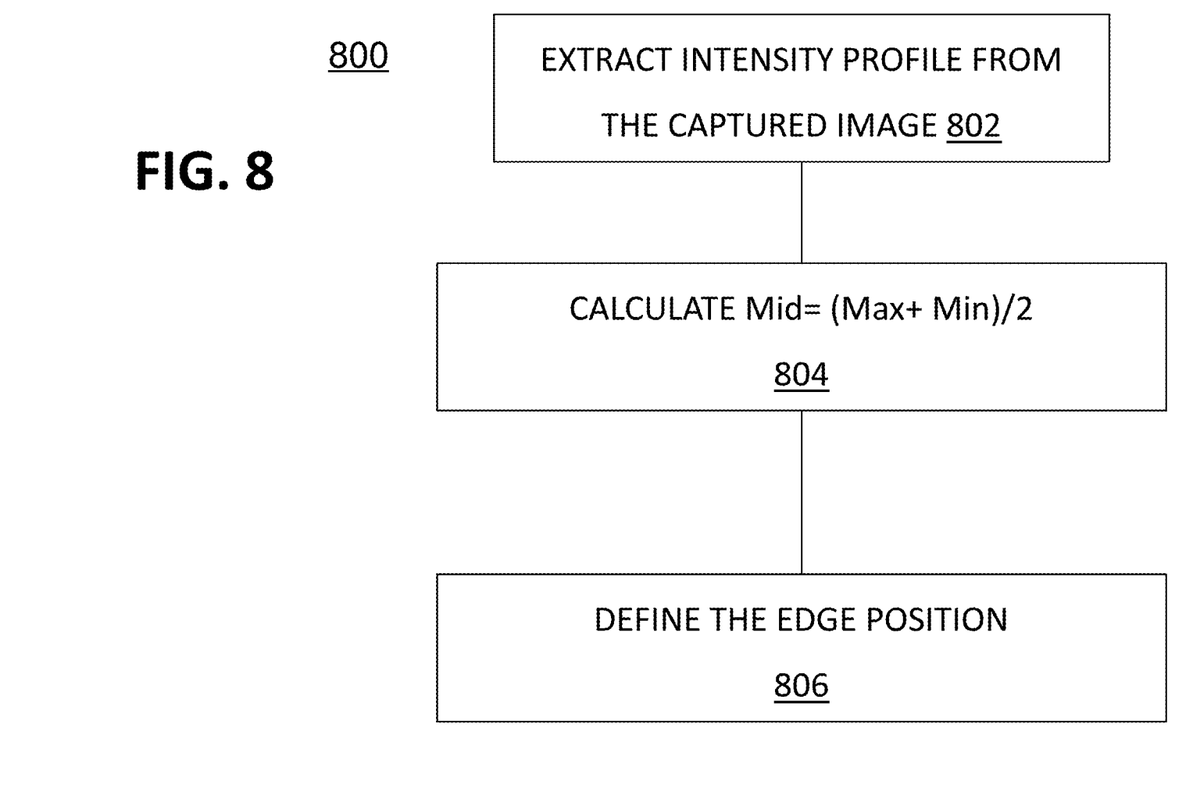
FIG. 8 is a flow diagram showing an optical edge tracking method.

Referring now briefly to FIG. 8, a flow diagram of an optical edge tracking method is shown. Here, the maximum color gradient 702 is defined as an "edge" and a new optical tracking technique is specially designed for the colorimetric sensing to determine the edge position by the following steps: 1) Extract intensity profile from the captured image by CMOS imager 802; 2) Find the maximum and the minimum intensity value along the sensor and calculate Mid=(Max+Min)/2 804; 3) Track the positions along the sensor that has the closest intensity value to Mid and define that position as the edge position 806.

FIG. 7A shows edge position defined by the tracking method. To validate this method for continuously tracking the $O_3$ concentration, the micro-colorimetric $O_3$ sensor was calibrated based on the edge moving speed at various concentrations of $O_3$. The results show a linear dependence of the edge moving speed on $O_3$ concentration over a large concentration range, from 0 to 500 ppbV. This concentration range covers most of the personal $O_3$ exposure monitoring applications. From the slope of the calibration, the sensitivity of the $O_3$ sensor was determined to be, slope= $(1.1409\pm0.06491)\times10^{-7}$ mm/s ($R^2$=0.98727). The detection limit of the sensor was determined by the noise in the measurement, $5.4933\times10^{-5}$ mm, corresponding to an $O_3$ detection limit of 440 ppb per second and 7 ppb per minute.

Referring now to FIG. 7B, an example of calibration of the micro-colorimetric $O_3$ sensor with a reference $O_3$ analyzer, showing a linear dependence of the sensor response (edge moving speed) to $O_3$ concentration is shown. To further validate the sensor's capability for continuously $O_3$ sensing, the sensor responses to changing $O_3$ concentrations in a gas chamber were tested, and it was found that the measured $O_3$ concentrations by the micro-colorimetric sensor (using the calibration factor) are in good agreement with those by the reference $O_3$ analyzer (obtained from 2B Technologies, Inc.). The plot 710 shows edge moving speed (mm/s) on the Y-axis versus ozone concentration (ppb) on the x-axis. Measured data for edge moving speed 712 was fitted with a linear fit 714. The test also shows that the micro-colorimetric sensor responded quickly, limited only by how fast change the $O_3$ concentration in the test chamber could be changed. The lifetime of the sensor depends on concentration, which can be determined from the sensing capacity, which describes the maximum amount concentration of analyte a sensor can detect over a time interval. In the present $O_3$ sensor, the capacity was determined to be 7 ppmV·hour, indicating that it can continuously monitor 100 ppbV $O_3$ for 70 hours. The EPA $O_3$ exposure limit is 70 ppbV for 8 hours, and $O_3$ concentration in typical ambient air is usually much lower than the EPA standard [26].

Figure 9A:
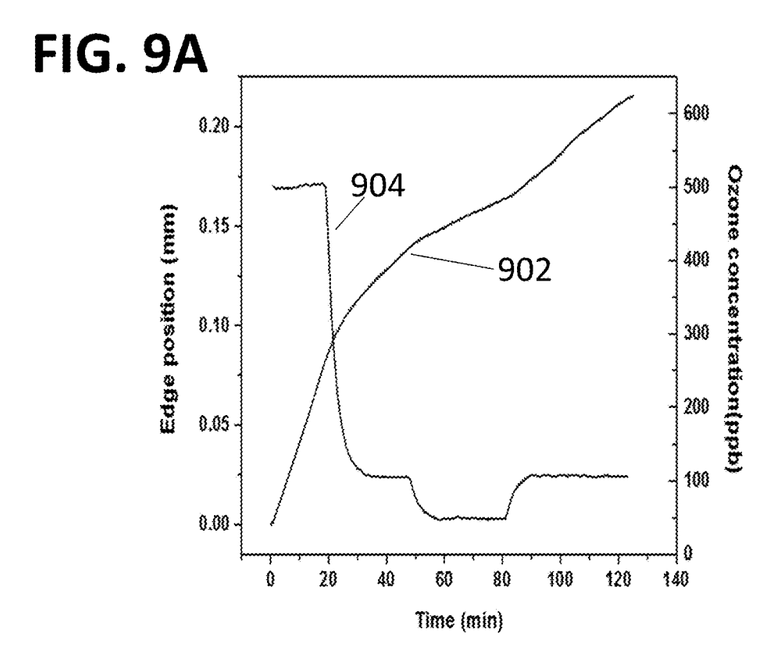
FIG. 9A shows an example of sensor responses to varying $O_3$ concentrations (25° C., 50% RH).

Referring now to FIG. 9A, an example of sensor responses to varying $O_3$ concentration (25° C., 50% RH) is shown. The selectivity of the $O_3$ sensor was tested by measuring the sensor responses to common pollutants in ambient air, including 100 ppbV nitrogen dioxide ($NO_2$), 1 ppmV ammonia ($NH_3$), 1 ppmV ethanol, 10 ppmV carbon monoxide (CO), 100 ppbV sulfur dioxide ($SO_2$), 100 ppbV formaldehyde (HCHO), and compared the response to 100 ppbV $O_3$. Curve 902 plots ozone concentration (ppb) against time in minutes. Curve 904 plots edge position (mm) against time in minutes.

Figure 9B:
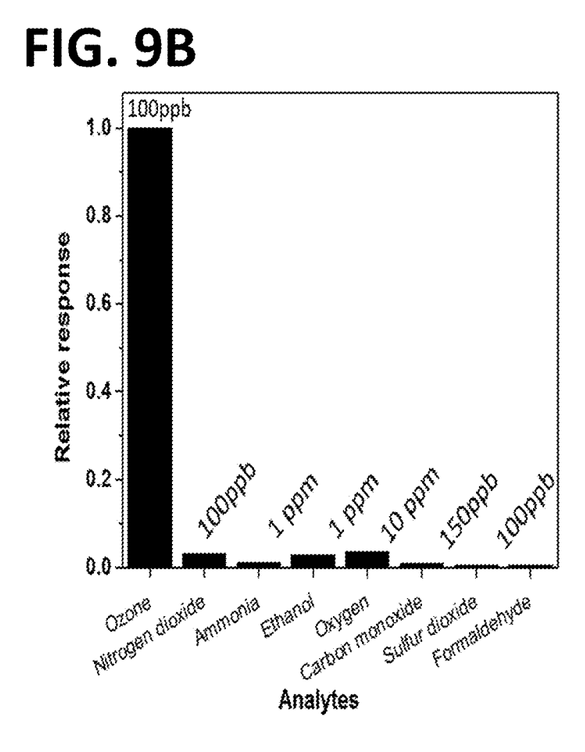
FIG. 9B shows data from a selectivity test with common interferents in the air ($NO_2$, $NH_3$, ethanol, CO, $SO_2$, and HCHO). The relative response was the sensor responses to these interferents normalized by that to $O_3$ at 100 ppbV. All

FIG. 9B data from a selectivity test with common interferents in the air ($NO_2$, $NH_3$, ethanol, CO, $SO_2$, and HCHO) is shown. The relative response was the sensor responses to these interferents normalized by that to $O_3$ at 100 ppbV. All of the responses are less than 5% response of 100 ppbV $O_3$, indicating that their interferences to $O_3$ detection are negligible. The excellent selectivity can be attributed to that $O_3$ reacts with indigo carmine strongly, producing a distinct change in the color.

Referring now to FIG. 10A, an example of an image of a micro-colorimetric sensor array showing color gradient developed on an $NO_2$ sensing channel after exposed to $NO_2$ is shown. The sensor array is embedded in a silica gel. Note that the sensor array can sense multiple chemicals including $NO_2$, $O_3$ and HCHO. There is a clear pattern of color spatial distribution to track for each chemical, namely, a sharp color gradient for each chemical, due to the fast gas diffusion through the air channel.

Referring now to FIG. 10B an example of an image of a micro-colorimetric sensor array showing color gradient developed on $O_3$ sensing channel after exposed to $O_3$ is shown. The sensor array is embedded in a silica gel. The sensor array is embedded in a silica gel. Note that the sensor array can sense multiple chemicals including $NO_2$, $O_3$ and HCHO. There is a clear pattern of color spatial distribution to track for each chemical, namely, a sharp color gradient for each chemical, due to the fast gas diffusion through the air channel.

Referring now to FIG. 10C an example of an image of a micro-colorimetric sensor array showing color gradient developed on HCHO sensing channel after exposed to HCHO is shown. The sensor array is embedded in a silica gel. The sensor array is embedded in a silica gel. Note that the sensor array can sense multiple chemicals including $NO_2$, $O_3$ and HCHO. There is a clear pattern of color spatial distribution to track for each chemical, namely, a sharp color gradient for each chemical, due to the fast gas diffusion through the air channel.

Various examples of a micro-colorimetric sensor have been described, these examples include a micro-colorimetric sensor having a substrate having a substrate top surface; a porous media coated on the substrate top surface, wherein the porous media includes a top surface; a plurality of sensing chemicals fused in parallel linear channels into the porous media; a means to determine a spatial distribution of color generated from the chemical reaction of analytes with the sensing material along each channel; a covering material affixed to the top surface of the porous media; and wherein each of the sensing chemicals is selected for a particular target chemical, so that the sensor can simultaneously detect multiple chemicals.

In one example, the spatial distribution of color comprises a gradient spatial distribution of color.

In one example, the means to determine a spatial distribution of color comprises a CMOS imager and an imaging processing algorithm to determine the spatial distribution of color and its change over time.

In another example, the imaging processing algorithm is selected from the group consisting of tracking intensity or absorbance change of the whole or part of the image, tracking the moving of intensity or absorbance pattern of the whole or part of the image where the pattern includes point, corner, edge, and block and combinations thereof.

In another example, the porous media is selected from the group consisting of silica gel, cellulose, polymers, porous glass, silicon, metal oxides, metal nitrides, zeolites and combinations thereof.

In another example, the sensing material is selected from the group consisting of materials adapted to sense airborne chemicals including $NO_2$, $NH_3$, ethanol, CO, $SO_2$, HCHO, and any combination thereof.

In another example, the porous media reacts with airborne chemicals to produce a color gradient reflecting the concentration of a target chemical.

In another example, a micro-colorimetric sensor, includes a substrate having a top surface; a plurality of parallel linear channels of porous media entrenched into the substrate, wherein each linear channel includes a sensing material adapted to sense one of several specific target chemicals in air; wherein each of the plurality of parallel linear channels is separated by barrier material from the adjacent parallel linear channel where the barrier material blocks diffusion of chemicals from one linear channel to another; a means to determine spatial distribution of color generated from the chemical reaction of analytes with the sensing material along each channel; and a plate affixed over the top surface of the substrate to cover the plurality of parallel linear channels.

In another example, and optical tracking method employing the micro-colorimetric sensor describe, wherein the micro-colorimetric sensor has an inlet, including diffusing an air sample from the inlet of the micro-colorimetric sensor; operating an imager to capture a plurality of color images of the micro-colorimetric sensor; tracking intensity or absorbance change of the whole or part of the image and tracking the moving of intensity or absorbance pattern of the whole or part of the image, the pattern includes point, corner, edge, and block.

Also described herein is a method of making a micro-colorimetric sensor by providing a substrate having a top surface; entrenching a plurality of parallel linear channels of porous media into the substrate; embedding a selected one of a plurality of sensing materials into each of the plurality of parallel linear channels, wherein each of the sensing materials are adapted to sense one of several specific target chemicals in air; separating the plurality of parallel linear channels is by barrier material from the adjacent parallel linear channel where the barrier material blocks diffusion of chemicals from one linear channel to another; a means to determine spatial distribution of color generated from the chemical reaction of analytes with the sensing material along each channel; and affixing a plate over the substrate top surface to cover the plurality of parallel linear channels so as to form a micro-colorimetric sensor having an inlet.

Certain exemplary embodiments of the invention have been described herein in considerable detail in order to comply with the Patent Statutes and to provide those skilled in the art with it the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publications are incorporated herein in their entirety by this reference.

1. Lim, S. S., et al., *A comparative risk assessment of burden of disease and injury attributable to 67 risk factors and risk factor clusters in 21 regions, 1990-2010: a systematic analysis for the Global Burden of Disease Study 2010.* The Lancet, 2012. 380(9859): p. 2224-2260.
2. Mills, N. L., et al., *Adverse cardiovascular effects of air pollution.* Nat. Clin. Pract. Cardiovasc. Med., 2009. 6(1): p. 36-44.
3. Saxon, A. and D. Diaz-Sanchez, *Air pollution and allergy: you are what you breathe.* Nat. Immunol., 2005. 6(3): p. 223-226.
4. Lelieveld, J., et al., *The contribution of outdoor air pollution sources to premature mortality on a global scale.* Nature, 2015. 525(7569): p. 367-371.
5. Xing, R., et al., *Preparation and Gas Sensing Properties of In2O3/Au Nanorods for Detection of Volatile Organic Compounds in Exhaled Breath.* Sci. Rep., 2015. 5: p. 10717.
6. Cui, S., et al., *Ultrahigh sensitivity and layer-dependent sensing performance of phosphorene-based gas sensors.* Nat. Commun., 2015. 6: p. 8632.
7. Tsujita, W., et al., *Gas sensor network for air-pollution monitoring.* Sens. Actuators, B, 2005. 110(2): p. 304-311.
8. Choi, S.-J., et al., *Selective Diagnosis of Diabetes Using Pt-Functionalized WO3 Hemitube Networks As a Sensing Layer of Acetone in Exhaled Breath.* Anal. Chem., 2013. 85(3): p. 1792-1796.
9. Mondal, S. P., et al., *Development of high sensitivity potentiometric NOx sensor and its application to breath analysis.* Sens. Actuators, B, 2011. 158(1): p. 292-298.
10. Yamazoe, N., *Toward innovations of gas sensor technology.* Sens. Actuators, B, 2005. 108(1): p. 2-14.
11. Li, J., et al., *Carbon Nanotube Sensors for Gas and Organic Vapor Detection.* Nano Lett., 2003. 3(7): p. 929-933.
12. Wetchakun, K., et al., *Semiconducting metal oxides as sensors for environmentally hazardous gases.* Sens. Actuators, B, 2011. 160(1): p. 580-591.
13. Kamionka, M., P. Breuil, and C. Pijolat, *Calibration of a multivariate gas sensing device for atmospheric pollution measurement.* Sens. Actuators, B, 2006. 118(1): p. 323-327.
14. Peterson, P., et al., *Practical Use of Metal Oxide Semiconductor Gas Sensors for Measuring Nitrogen Dioxide and Ozone in Urban Environments.* Sensors, 2017. 17(7): p. 1653.
15. Pang, X., et al., *Electrochemical ozone sensors: A miniaturised alternative for ozone measurements in laboratory experiments and air-quality monitoring.* Sens. Actuators, B, 2017. 240: p. 829-837.
16. Korotcenkov, G. and B. K. Cho, *Ozone measuring: What can limit application of SnO2-based conductometric gas sensors?* Sens. Actuators, B, 2012. 161(1): p. 28-44.
17. Dräger-Tube/CMS Handbook: *Handbook for short term measurements in soil, water and air investigations as well as technical gas analysis.* 16th Edition ed. 2011, Lübeck: Dräger Safety AG & Co KGaA. 225.
18. Rakow, N. A. and K. S. Suslick, *A colorimetric sensor array for odour visualization.* Nature, 2000. 406: p. 710.
19. Mazzone, P. J., et al., *Lung Cancer Diagnosis by the Analysis of Exhaled Breath with a Colorimetric Sensor Array.* Thorax, 2007.
20. Nakano, N. and K. Nagashima, *An automatic monitor of formaldehyde in air by a monitoring tape method.* Journal of Environmental Monitoring, 1999. 1(3): p. 255-258.
21. Tsow, F., E. S. Forzani, and N. Tao, *Frequency-coded chemical sensors.* Analytical chemistry, 2008. 80(3): p. 606-611.
22. Wang, R., et al., *A microfluidic-colorimetric sensor for continuous monitoring of reactive environmental chemicals.* IEEE Sensors Journal, 2012. 12(5): p. 1529-1535.
23. Qin, X., et al., *A colorimetric chemical sensing platform for real-time monitoring of indoor formaldehyde.* IEEE Sensors Journal, 2015. 15(3): p. 1545-1551.
24. Heckmann, J., *Colorimetric gas measuring device.* 1990, Google Patents.
25. Takeuchi, K. and T. Ibusuki, *Quantitative determination of aqueous-phase ozone by chemiluminescence using indigo-5, 5'-disulfonate.* Analytical chemistry, 1989. 61(6): p. 619-623.
26. United States Environmental Protection Agency. *National Ambient Air Quality Standards Table.* https://www.epa.gov/criteria-airpollutants/naaqs-table #3 2016.
27. Guan, Y., et al., *Kinetics of small molecule interactions with membrane proteins in single cells measured with mechanical amplification.* Science advances, 2015. 1(9): p. e1500633.
28. Wang, H., et al., *Determining electrochemical surface stress of single nanowires.* Angewandte Chemie International Edition, 2017. 56(8): p. 2132-2135.

What is claimed is:

1. A micro-colorimetric sensor comprising:
a substrate having a substrate top surface;
a plurality of parallel linear trenches defined in the substrate and recessed relative to the substrate top surface, each parallel linear trench having an inlet end and an outlet end;
a cover plate affixed to the substrate top surface to contact areas of the substrate top surface between linear trenches of plurality of parallel linear trenches;
a porous media with an embedded plurality of sensing materials that fills the plurality of parallel linear trenches to form a micro-colorimetric sensor array;
wherein, during use of the micro-colorimetric sensor, the substrate and the cover plate cooperate to form barriers between the plurality of parallel linear trenches to eliminate chemical diffusion from one of the plurality of parallel linear trenches to another;
wherein the micro-colorimetric sensor array is configured to receive air samples at the inlet ends of the parallel linear trenches and permit the air samples to diffuse through the porous media, confined between the substrate and the cover plate, in a direction towards the outlet ends and produce a plurality of color images generated from a chemical reaction of analytes with the plurality of sensing materials; and
wherein the plurality of sensing materials is selected for one or more target chemicals.

2. The micro-colorimetric sensor of claim 1 wherein the plurality of color images generates a spatial distribution of color.

3. The micro-colorimetric sensor of claim 1 wherein the micro-colorimetric sensor array is optically coupled to an imager that is coupled to an optical lens.

4. The micro-colorimetric sensor of claim 1 wherein the porous media is selected from the group consisting of silica gel, cellulose, polymers, porous glass, silicon, metal oxides, metal nitrides, zeolites and combinations thereof.

5. The micro-colorimetric sensor of claim 4 wherein the plurality of sensing materials is selected from the group consisting of materials adapted to sense airborne chemicals including $NO_2$, $NH_3$, ethanol, CO, $SO_2$, HCHO, and any combination thereof.

6. The micro-colorimetric sensor of claim 5 wherein the porous media reacts with airborne chemicals to produce a color gradient representing a concentration of a selected one of the one or more target chemicals.

7. The micro-colorimetric sensor of claim 1, wherein the inlet end of each parallel linear trench is positioned along and between adjacent lateral edges of the substrate and the cover plate.

8. A micro-colorimetric sensor comprising:
a substrate having a substrate top surface;
a plurality of parallel linear trenches defined in the substrate top surface and recessed relative to the substrate top surface, with the substrate forming a plurality of parallel barriers separating adjacent parallel linear trenches, and with each parallel linear trench having an inlet end and an outlet end;
a cover plate affixed over the substrate top surface to cover the plurality of parallel linear trenches, wherein during use of the micro-colorimetric sensor, the cover plate contacts areas of the substrate top surface between linear trenches of the plurality of parallel linear trenches, and wherein the substrate and cover plate cooperate to form barriers between the plurality of parallel linear trenches to eliminate chemical diffusion from one of the plurality of parallel linear trenches to another;
a porous media substantially filling each of the plurality of parallel linear trenches, wherein each of the plurality of parallel linear trenches includes a sensing material adapted to sense a specific target chemical;
wherein the micro-colorimetric sensor is configured to receive air samples at the inlet ends of the parallel linear trenches and permit the air samples to diffuse through the porous media, confined between the substrate and the cover plate, in a direction towards the outlet ends; and
wherein the micro-colorimetric sensor further comprises an imager configured to produce a plurality of color images generated from a chemical reaction of analytes in the air samples with the sensing material.

9. The micro-colorimetric sensor of claim 8 wherein the plurality of color images generates a spatial distribution of color.

10. The micro-colorimetric sensor of claim 8 wherein the porous media is selected from the group consisting of silica gel, cellulose, polymers, porous glass, silicon, metal oxides, metal nitrides, zeolites and combinations thereof.

11. The micro-colorimetric sensor of claim 8 wherein the sensing material is selected from the group consisting of materials adapted to sense airborne chemicals including $NO_2$, $NH_3$, ethanol, CO, $SO_2$, HCHO, and combinations thereof.

12. The micro-colorimetric sensor of claim 8 wherein the sensing material is loaded in the porous media and reacts with airborne chemicals to produce a color gradient along the micro-colorimetric sensor.

13. The micro-colorimetric sensor of claim 8, wherein the inlet end of each parallel linear trench is positioned along and between adjacent lateral edges of the substrate and the cover plate.

14. An optical tracking method employing the micro-colorimetric sensor of claim 3 or 8, comprising:
diffusing an air sample from an inlet of the micro-colorimetric sensor;
operating the imager to capture the plurality of color images of the micro-colorimetric sensor; and
tracking an intensity or an absorbance change of the at least a part of each color image and tracking a moving of intensity or an absorbance pattern of at least a part of each color image, wherein the intensity or absorbance pattern includes point, corner, edge, and block.

15. The optical tracking method of claim 14, wherein the tracking of an intensity or an absorbance change of each color image and tracking of moving of an intensity or absorbance change of each color image comprises:
extracting an intensity profile from each color image,
finding a maximum and minimum intensity value for each color image,
calculating Mid=(Max+Min)/2 from the maximum and minimum intensity values, and
defining an edge position having an intensity value closest to Mid.

* * * * *